(12) United States Patent
Taller et al.

(10) Patent No.: US 7,408,762 B2
(45) Date of Patent: Aug. 5, 2008

(54) METHOD AND APPARATUS FOR PROVIDING CAPACITOR FEEDTHROUGH

(75) Inventors: James A. Taller, White Bear Lake, MN (US); Michael J. O'Phelan, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 214 days.

(21) Appl. No.: 11/182,729

(22) Filed: Jul. 15, 2005

(65) Prior Publication Data
US 2006/0017089 A1   Jan. 26, 2006

Related U.S. Application Data

(60) Provisional application No. 60/588,811, filed on Jul. 16, 2004.

(51) Int. Cl.
  *H01G 4/35* (2006.01)
(52) U.S. Cl. ............... 361/302; 361/303; 361/305; 361/508; 361/509; 361/525; 607/5; 607/7
(58) Field of Classification Search ......... 361/302–305, 361/508–512, 516–519, 523–534; 607/5, 607/7
See application file for complete search history.

(56) References Cited

U.S. PATENT DOCUMENTS

| | | | |
|---|---|---|---|
| 3,489,266 A | 1/1970 | Miller | |
| 4,243,042 A | 1/1981 | Ware | |
| 4,252,873 A | 2/1981 | Epstein et al. | |
| 4,324,847 A | 4/1982 | Athearn | |
| 5,131,388 A | 7/1992 | Pless et al. | |
| 5,173,375 A | 12/1992 | Cretzmeyer et al. | |
| 5,250,373 A | 10/1993 | Muffoletto et al. | |
| 5,423,334 A | 6/1995 | Jordan | |
| 5,434,017 A | 7/1995 | Berkowitz et al. | |
| 5,759,668 A | 6/1998 | Ischikawa et al. | |
| 5,926,362 A | 7/1999 | Muffoletto et al. | |
| 6,010,803 A | 1/2000 | Heller et al. | |
| 6,117,195 A | 9/2000 | Honegger | |
| 6,184,160 B1 * | 2/2001 | Yan et al. ............. 438/800 |
| 6,191,931 B1 | 2/2001 | Paspa et al. | |

(Continued)

OTHER PUBLICATIONS

Non-Final Office Action mailed by the USPTO on Feb. 2, 2006 for related matter U.S. Appl. No. 11/183,235, 10 Pages.

(Continued)

*Primary Examiner*—Nguyen T. Ha
(74) *Attorney, Agent, or Firm*—Schwegman, Lundberg & Woessner, P.A.

(57) ABSTRACT

A capacitor feedthrough assembly with a cavity including a capacitor stack, including one or more substantially flat anode layers and one or more substantially flat cathode layers in a case with a cover, the case having a first opening sized for passage of the capacitor stack and a second opening defined by a lip. Additionally, the capacitor includes a conductive member attached to the capacitor stack and disposed at least part way through the second opening in the case, and an isolating element disposed between the lip and at least a portion of the connected stack and conductive member. Also, the capacitor includes a curable resin sealingly disposed in the cavity defined by the second opening, the isolating element, and the conductive member, the curable resin electrically isolating the case from the conductive member.

29 Claims, 7 Drawing Sheets

U.S. PATENT DOCUMENTS

| | | | |
|---|---|---|---|
| 6,334,879 B1 | 1/2002 | Muffoletto et al. | |
| 6,338,284 B1 * | 1/2002 | Najafi et al. | 73/866.1 |
| 6,388,866 B1 | 5/2002 | Rorvick et al. | |
| 6,402,793 B1 | 6/2002 | Miltich et al. | |
| 6,409,776 B1 * | 6/2002 | Yan et al. | 29/25.03 |
| 6,430,031 B1 | 8/2002 | Dispennette et al. | |
| 6,459,566 B1 | 10/2002 | Casby et al. | |
| 6,477,037 B1 * | 11/2002 | Nielsen et al. | 361/520 |
| 6,493,212 B1 * | 12/2002 | Clarke et al. | 361/521 |
| 6,498,951 B1 | 12/2002 | Larson et al. | |
| 6,602,742 B2 | 8/2003 | Maletin et al. | |
| 6,610,443 B2 | 8/2003 | Paulot et al. | |
| 6,613,474 B2 | 9/2003 | Frustaci et al. | |
| 6,628,505 B1 * | 9/2003 | Andelman | 361/541 |
| 6,643,903 B2 * | 11/2003 | Stevenson et al. | 29/25.42 |
| 6,648,928 B2 | 11/2003 | Nielsen et al. | |
| 6,678,559 B1 | 1/2004 | Breyen et al. | |
| 6,699,265 B1 | 3/2004 | O'Phelan et al. | |
| 6,709,946 B2 * | 3/2004 | O'Phelan et al. | 438/396 |
| 6,801,424 B1 | 10/2004 | Nielsen et al. | |
| 6,807,048 B1 | 10/2004 | Nielsen et al. | |
| 6,819,544 B1 | 11/2004 | Nielsen et al. | |
| 6,836,683 B2 | 12/2004 | Nielsen et al. | |
| 6,842,328 B2 | 1/2005 | Schott et al. | |
| 6,859,353 B2 | 2/2005 | Elliott et al. | |
| 6,922,330 B2 | 7/2005 | Nielsen et al. | |
| 7,164,574 B2 | 1/2007 | Barr et al. | |
| 2001/0049057 A1 | 12/2001 | Frustaci et al. | |
| 2003/0017372 A1 | 1/2003 | Probst et al. | |
| 2004/0018425 A1 | 1/2004 | Kejha et al. | |
| 2004/0240153 A1 | 12/2004 | Nielsen et al. | |
| 2004/0258988 A1 | 12/2004 | Nielsen et al. | |
| 2004/0260354 A1 | 12/2004 | Nielsen et al. | |
| 2005/0002147 A1 | 1/2005 | Nielsen et al. | |
| 2005/0112460 A1 | 5/2005 | Howard et al. | |
| 2005/0162810 A1 | 7/2005 | Seitz et al. | |
| 2005/0190530 A1 | 9/2005 | Muffoletto et al. | |
| 2006/0018079 A1 | 1/2006 | Barr et al. | |
| 2006/0018083 A1 | 1/2006 | Schmidt | |
| 2007/0097600 A1 | 5/2007 | Barr et al. | |

OTHER PUBLICATIONS

Non-Final Office Action Response Filed May 16, 2006 with the USPTO for related matter U.S. Appl. No. 11/183,235, 11 Pages.

"U.S. Appl. No. 11/183,235, Amendment and Response filed Jan. 24, 2006 to Ex Parte Quayle Office Action mailed Nov. 25, 2005", 4 pgs.

"U.S. Appl. No. 11/183,235, Ex Parte Quayle Office Action mailed Nov. 25, 2005", 5 pgs.

"U.S. Appl. No. 11/183,235, Interview Summary mailed Oct. 18, 2006", 1 pg.

"U.S. Appl. No. 11/183,235, Notice of Allowance mailed Jun. 7, 2006", 6 pgs.

"U.S. Appl. No. 11/183,235, Notice of Allowance mailed Aug. 22, 2006", 4 pgs.

"U.S. Appl. No. 11/183,235, Supplemental Notice of Allowability mailed Oct. 18, 2006", 5 pgs.

"U.S. Appl. No. 11/567,940, Response files May 30, 2007 to Restriction Requirement mailed May 1, 2007", 8 pgs.

"U.S. Appl. No. 11/567,940, Restriction Requirement mailed May 1, 2007", 5 pgs.

"U.S. Appl. No. 11/567,940, Non-Final Office Action mailed Aug. 24, 2007", 14 pgs.

* cited by examiner

METHOD AND APPARATUS FOR
PROVIDING CAPACITOR FEEDTHROUGH

CLAIM OF BENEFIT OF PRIOR-FILED APPLICATION

This patent application claims the benefit of U.S. Provisional Application Ser. No. 60/588,811, entitled "Method and Apparatus for Openings in a Capacitor Case," filed on Jul. 16, 2004.

FIELD OF THE INVENTION

This disclosure relates generally to capacitors, and more particularly, to compact, electrolytic, flat high voltage electrolytic capacitors made from substantially planar layers.

BACKGROUND

A capacitor is an electric circuit element used to store charge temporarily, consisting in general of two metallic plates separated and insulated from each other by a dielectric. Capacitors are useful as a compact source for a high energy pulse.

In many instances, the capacitor takes the form of an aluminum electrolytic capacitor. Existing designs include one or more separators disposed between two or more sheets of aluminum foil. One of the foils serves as the anode of the capacitor, and the other serves as the cathode. Some designs include multiple foils which are interconnected to increase effective size of the anode or cathode.

Varying devices benefit from compact capacitor designs. Implantable cardioverter defibrillators are typically implanted in the left region of the chest or in the abdomen, and include a housing and one or more leads implanted in the patient. Existing implantable cardioverter defibrillator designs include capacitors which can consume 30% of the volume of the housing. A need exists for a smaller device which is capable of delivering patient therapy. One way to obtain a smaller device is to reduce capacitor size. Capacitor size can be reduced through a reduction in capacitor component size. Making a capacitor case thinner is one way to reduce capacitor size.

However, a thin case can raise additional issues. For example, thin cases increase manufacturing difficulty. Increased manufacturing difficulty can result in higher costs. What is needed is a case which is thin, and which is compatible with a variety of manufacturing processes.

SUMMARY

The above-mentioned problems and others not expressly discussed herein are addressed by the present subject matter and will be understood by reading and studying this specification.

In varying embodiments, the present subject matter includes an apparatus, comprising a capacitor stack, including one or more substantially planar anode layers, and one or more substantially planar cathode layers, a case having a first opening and a second opening, the first opening sized for passage of the capacitor stack; the second opening defined by walls having a first thickness, a cover substantially conforming to the first opening and sealingly connected to the first opening, a plate substantially conforming to the second opening, the plate sealingly connected to the second opening, the plate having a second thickness which is approximately greater than the first thickness of the walls defining the second opening, and a terminal connected to the plate. Additionally, the present subject matter includes embodiments wherein the capacitor stack is disposed in the case, and the terminal is in electrical connection with the case and at least one capacitor electrode.

Also, the present subject matter includes a method, comprising assembling a capacitor stack out of electrodes which conform approximately to planar shapes, placing the capacitor stack in a case with a first opening and a second opening, the first opening sized for the passage of the capacitor stack, the second opening defined by walls having a first thickness, inserting a plate in the second opening from the inside of the case, the plate substantially conforming to the second opening, the plate having a second thickness which is approximately greater than the first thickness of the walls defining the second opening, sealing the plate to the case, and attaching a terminal to the plate.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. It will be apparent, however, to one skilled in the art that the various embodiments may be practiced without some of these specific details. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
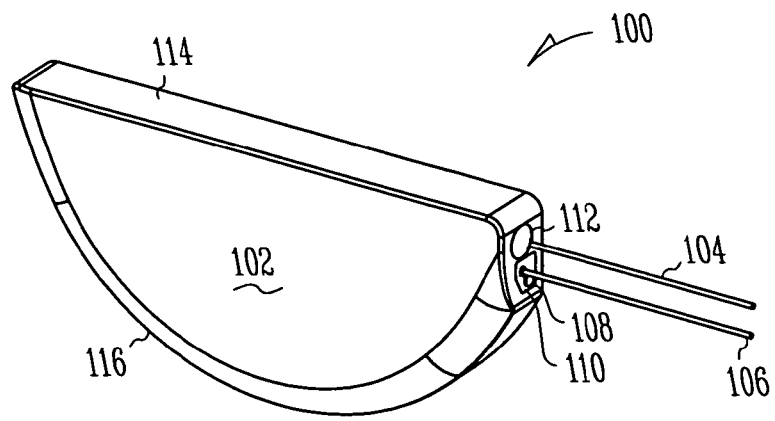
FIG. 1 shows a flat capacitor according to one embodiment of the present subject matter.

FIG. 1 shows a flat capacitor 100, according to one embodiment of the present subject matter. The capacitor pictured is useful in a variety of applications, including as a power source to provide electrical stimulation in implantable cardioverter defibrillators. In various embodiments, the capacitor is connected to other components, including one or more leads which conduct energy from the implantable cardioverter defibrillator to the patient, a battery to charge the capacitor, and circuitry used to control the capacitor and to monitor the patient.

Capacitors must include at least one anode element and at least one cathode element, but are not constrained to one shape by design. Various examples of capacitors use a set of interconnected anode electrode elements and a set of interconnected cathode electrode elements. The present subject matter includes, in various embodiments, capacitors which are substantially planar, or flat, in shape, comprising anode and cathode elements placed into a stack. One example of a capacitor stack is disclosed in U.S. Pat. No. 6,699,265 to O'Phalen, et al., which is assigned to a common assignee and is incorporated here by reference. Capacitors which are substantially planar, in various embodiments, offer a geometry which is beneficial for packaging. Substantially planar capacitors offer additional benefits as well, such as improved performance and manufacturing efficiency. It should be noted, however, that although capacitor 100 is D-shaped and substantially planar, in varying embodiments, the capacitor is shaped differently, including other symmetrical or asymmetrical shapes.

Capacitor 100 includes a case, which in some embodiments includes at least two components; a substantially flat surface and connected sidewalls which form a cup-shaped receptacle, and a substantially flat cover. In various embodiments, the case has one or more openings, and the cover conforms to one of the openings. In one embodiment, the cover is located approximately parallel to substantially planar surface 102. In one embodiment, the case 114 includes a curvature 116 which allows the case to be placed in receptacles which conform to the curvature. Among other benefits, the case is useful to retain electrolyte in capacitors using a fluidic electrolyte. In other words, various examples of the present subject matter comprise flat capacitors with a number of electrodes stacked and placed in a case, with the case filled with electrolyte.

It should be noted that in various embodiments, the case and cover include openings which are formed, in part, by features present in one or both the cover and the case. For example, in one embodiment, the cup-shaped receptacle includes a semi-circle shaped edge discontinuity, and the cover includes a semi-circle edge discontinuity, and when they are assembled, they form a circle shaped opening in a case.

In accordance with the design requirement of retaining electrolyte, in various examples, the case and the cover mate to form a seal. Varying embodiments use welding to join the case and the cover. For example, in one embodiment, the cover is laser welded to the case 114. In one embodiment, the weld is performed by an approximately 1064 nm Yag laser having an energy range of approximately 2.5 joules to 3.5 joules. Other embodiments use mechanical locks to join the cover and case, or various forms of adhesive. Some embodiments use a combination of known joining methods, including crimping combined with welding. Preferred designs form a seal between the case and the cover which resists the flow of electrolyte.

In various embodiments, the capacitor of the present invention includes an anode conductor 104 and a cathode conductor 106. In various embodiments, these conductors connect the anode of the capacitor stack and the cathode of the capacitor stack with electronics which are located external to the capacitor. In various embodiments, one or both of these conductors are electrically isolated from the capacitor case. In one example, the case 114 of the capacitor is electrically conductive and comprises a portion of the cathode. This exemplary variant is manufactured from aluminum, and is connected to the cathode of the capacitor stack using a connection means internal to the case 114. In other embodiments, the case is manufactured using a nonconductive material, such as a ceramic or a plastic. It should be noted that the case can also comprise a portion of the anode.

In embodiments where the capacitor case forms part of a set of capacitor electrodes, one way to economically connect a conductor to the desired portions of the capacitor stack is to connect the conductor directly to the exterior of the case. In various embodiments, attaching an electrode to the case is facilitated by a plate. One example uses a plate 110 which is electrically conductive, and which is laser welded to the case 114, placing the plate 110 in electrical communication with the case 114. In one embodiment, the weld is performed by an approximately 1064 nm Yag laser weld with an energy range of approximately 1.5 joules to 2.5 joules. The seal formed by welding a plate to a case, in various embodiments, is sufficient to restrict the flow of electrolyte. In one example, cathode conductor 106 is arc percussion welded to the plate 110. In further embodiments, the weld connection is formed using resistance welding.

In one example, a conductor is held to a plate with a clamping force of from about 5 to 15 pounds. In the example, the welding process uses a current of from about 350 to 500 Amps. The ramp time in the example is from about 5 to 15 milliseconds. The time for the weld in the example is from about 5 to 15 milliseconds. The gas flow for the example process is from about 0 to 8 standard cubic feet per hour.

Welding processes, including those taught herein, result in conductor 106 being placed in electrical communication with a capacitor stack located inside the case. In other words, in one embodiment, the cathode conductor 106 is percussion welded to the plate 110, which is laser welded to the case 114, which is in electrical communication with the cathode of the capacitor stack placed inside the case 114.

Additionally, in various examples, the plate includes an aperture sealed by a plug. In one example, a plug 108 is laser welded to the plate 110. In one embodiment, the weld is performed by an approximately 1064 nm Yag laser weld with an energy range of approximately 1.5 joules to 2.5 joules. In varying embodiments, the plug and aperture are used to fill the capacitor case with electrolyte. The seal formed by welding the plug to the plate is, in some examples, sufficient to restrict the flow of electrolyte.

Varying embodiments of the present subject matter include a conductor feedthrough in the case. In various embodiments, a feedthrough enables a conductor to provide a conductive path from the exterior of the case to the interior of the case, without conducting electricity to the case. An exemplary embodiment includes a cathodic case 114 and uses a feedthrough to put the anode of the capacitor stack in electrical communication with electronics external to the case 114, in a manner isolated from the cathodic case. The example uses the anode conductor 104, which passes through the feedthrough, to conduct electricity. Because the feedthrough passageway comprises a hole in the case, in embodiments where the capacitor is filled with electrolyte, the feedthrough passageway must be sealed. To seal the feedthrough passage, various examples include a curable resin disposed between the case and the conductor, the curable resin conforming to the feedthrough passage, and resisting the flow of electrolyte. In one example, the curable resin 112 is an epoxy conforming to the feedthrough passageway and bonded to the anode conductor 104 and the case 114. Varying embodiments form a hermetic seal.

Overall, the present subject matter enables various improvements over the current art. For example, by eliminating the need to pass one or more conductors through the case by directly connecting the conductor to the plate, the cost of capacitor manufacturing can be reduced, and complexity affecting reliability and manufacturing can be reduced. By using a plate, a capacitor design can include a case of varying thicknesses. In one embodiment, the thickness of the insert plate is 0.030 inches. In varying embodiments, insert plates run from approximately 0.020 inches thick to 0.040 inches thick. In varying embodiments, the insert plate is combined with a case this is approximately 0.010 inches thick. Additionally, in one embodiments, a case which is from about 0.008 inches thick to about 0.015 inches thick.

For example, in one embodiment, the plate mounts coplanar to the exterior of the case, but extends into the capacitor deeper than does the thickness of the case 114. One benefit of this design is that a welding process for connecting a conductor to the case may be used which requires material thickness greater than that of the case 114. For example, one embodiment uses arc percussion welding with parameters which are sufficient to weld a conductor to the plate 110, but which would damage the case 114 if the conductor were welded to the case 114. In further embodiments, the weld connection is formed using resistance welding.

In one example, a conductor is held to a plate with a clamping force of from about 5 to 15 pounds. In the example, the welding process uses a current of from about 350 to 500 Amps. The ramp time in the example is from about 5 to 15 milliseconds. The time for the weld in the example is from about 5 to 15 milliseconds. The gas flow for the example process is from about 0 to 8 standard cubic feet per hour.

As such, the present subject matter allows using a capacitor with a case which is too thin for some metal bonding processes, but which is otherwise sufficient to satisfy other requirements of the case, such as retaining electrolyte and a capacitor stack. This design, in various embodiments, allows for a reduction in case thickness and mass, without sacrificing welding options available for connecting the conductor to the capacitor, ultimately providing for a smaller capacitor, and therefore, for a smaller implantable device.

Figure 2:
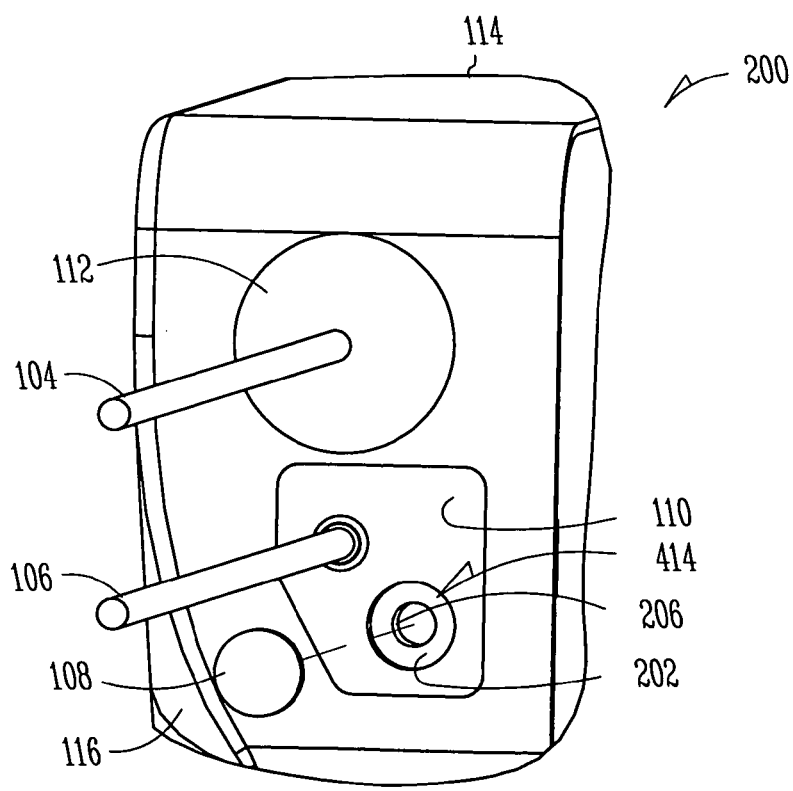
FIG. 2 illustrates a close up view of the plate and plug of FIG. 1.

FIG. 2 illustrates a close up view 200 of the plate and plug of FIG. 1, according to one embodiment of the present subject matter. In various embodiments, the capacitor includes case 114. In one embodiment, the case includes a curvature 116 which is adapted to allow the capacitor to be placed in a similarly shaped receptacle. The example also includes a cathode conductor 106, an anode conductor 104, a curable resin 112, a plate 110, and a plug 108. Additionally, various embodiments include an aperture which extends from the exterior of the case to the interior of the case, and which, in some examples, passes through the plate.

In one exemplary embodiment, plate 110 is welded to case 114 forming a seal which restricts the flow of electrolyte. Similarly, the aperture 414 is sealed and resists the flow of electrolyte by welding the plug 108 to the plate 110, in various embodiments of the present subject matter. It should be noted that in other embodiments of the present subject matter, the plate is fastened to the case with other fastening means, including a physical lock such as threads. Additionally, the plug 108 is fastened to the plate with alternate fastening means, such as threads. These and other types of fastening designs are within the scope of the present subject matter, and the list enumerated here is not intended to be limiting.

Figure 3:
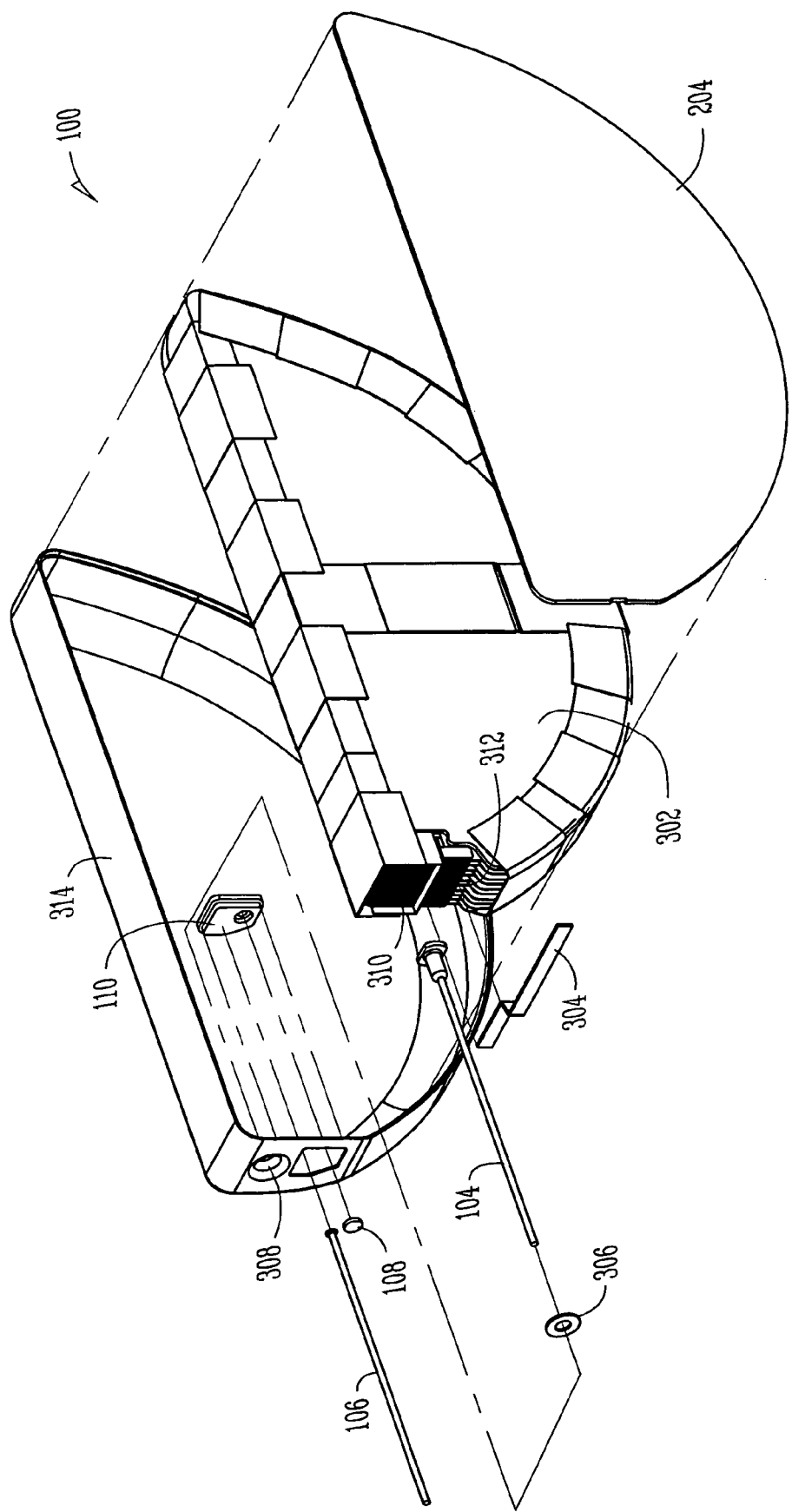
FIG. 3 illustrates an exploded view of a capacitor, according to one embodiment of the present subject matter.

FIG. 3 illustrates an exploded view of a capacitor 100, according to one embodiment of the present subject matter. In various embodiments, cup shaped receptacle 314 includes a feedthrough passageway 308 which is formed in a sidewall of the cup shaped receptacle 314. Additionally, a cover 204 is adapted for conforming to an opening in the cup shaped receptacle 314 of the case 114. The feedthrough passageway 308, in various embodiments, is useful to allow the passage of a conductor which connects external circuitry at one end to a capacitor stack at the other. Additionally, in various embodiments, a paper isolating element 306 is placed proximal to the feedthrough passageway 308, and internal to the case. For example, in one embodiment, the anode conductor 104 passes through the case and connects to the anode of the capacitor stack 302. In some embodiments, case 114 includes two or more feedthrough passageways.

Internal to various embodiments of the assembled capacitor is a terminal 304, which is connected to the capacitor stack 302 and to one of the group including the cup shaped receptacle 314, the cover 204, or both the cup shaped receptacle 314 and the cover 204. In various embodiments, a connection between the terminal 304 and the cover 204 is formed by pinching the terminal 304 during assembly of the capacitor stack 302, the cup-shaped receptacle 314, and the cover 204. Various embodiments connect terminal 314 to the electrode stack 302 using additional means, such as welding.

In one example, the cathode conductor 106 is connected to the plate 110, which is connected to the cup shaped receptacle, which is connected to terminal 304, which is connected to the cathode of the capacitor stack 302. Additionally, a plug 108 is attached to the plate 110.

The capacitor stack 302, in various embodiments, is constructed in a shape which approximates the interior space in the receptacle, in order to reduce unused space, which can reduce capacitor size, and concomitantly, device size. One method of reducing device size includes choosing components in the capacitor stack to adjust the physical dimensions of the capacitor stack 302. For example, in one embodiment, anode layers are added or subtracted from the stack, resulting in a capacitor stack 302 which matches the interior volume of a particular case. In this exemplary embodiment, the capacitor stack includes 20 cathode layers, and 58 anode layers, but it should be understood that other embodiments include different numbers of elements.

Figure 4A:
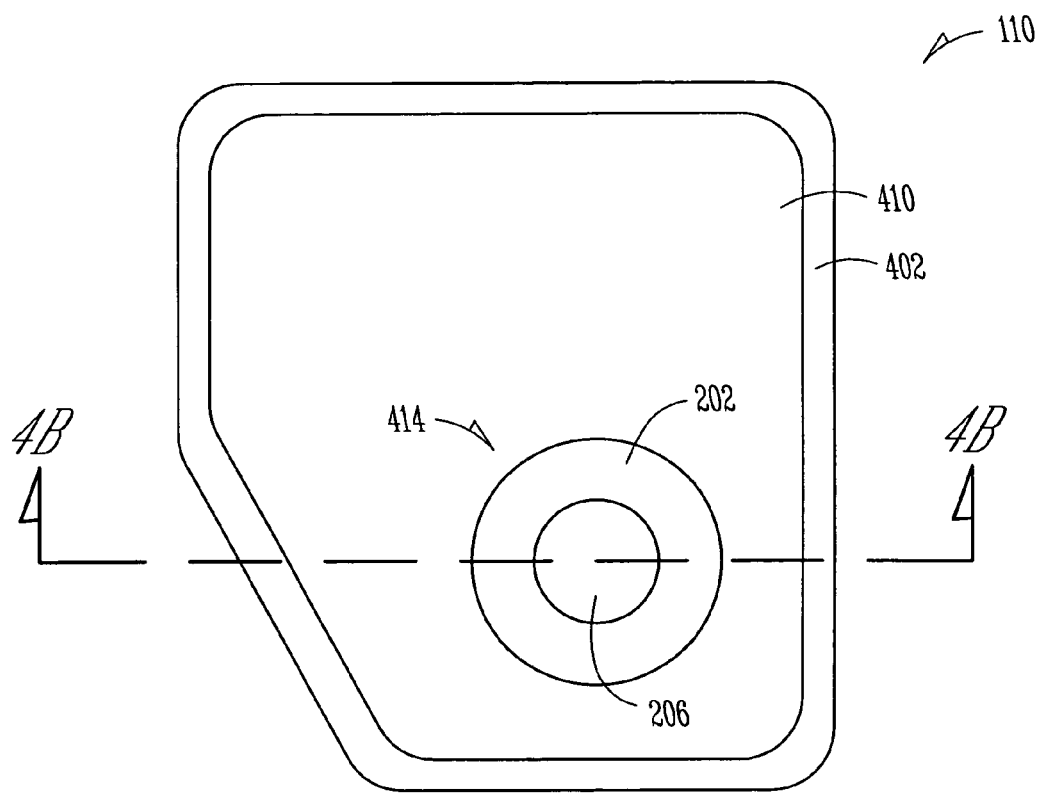
FIG. 4A illustrates the front view of a plate, according to one embodiment of the present subject matter.

FIG. 4A illustrates the front view of a plate 110, according to one embodiment of the present subject matter. In various embodiments, the plate 110 includes an aperture 414. Some embodiments include an aperture 414 with a first portion 202, and a second portion 206. Various embodiments of the first portion 202 and the second portion 206 comprise coaxial cylindrical shapes with varying diameters. Additionally, various embodiments of the plate include a first major surface 410.

In various embodiments, the plate 110 is shaped like an irregular pentagon with three rounded adjacent apexes which are approximately 90 degrees, and two rounded adjacent apexes which are obtuse angles. However, it should be noted that other plate shapes are within the scope of the present subject matter.

Figure 4B:
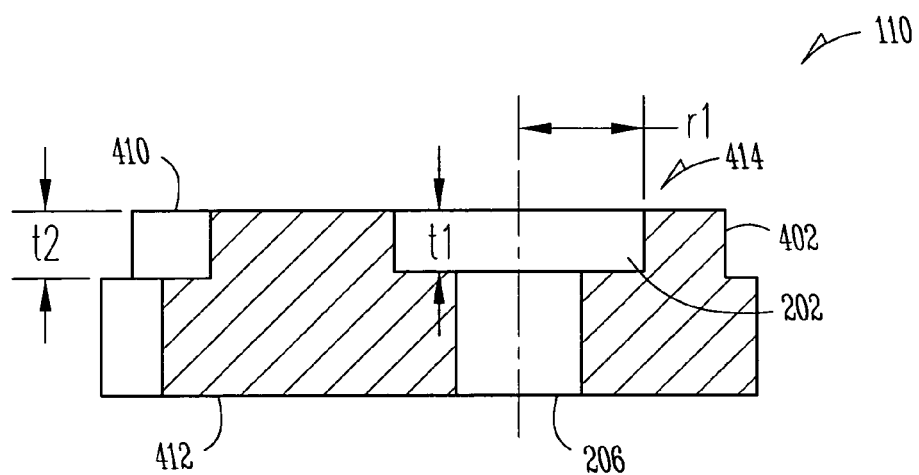
FIG. 4B illustrates a cross section taken at line 4B-4B of FIG. 4A.

FIG. 4B illustrates a cross section taken at line 4B-4B of FIG. 4A. In various embodiments, the aperture 414 includes a first portion 202. Various examples of the aperture 414 are shaped like a counterbore, with the first portion 202 comprising a larger diameter, the second portion comprising a smaller diameter, and the difference between the two diameters comprising a substantially planar step shape defined by the concentric circles of the perimeters of the first and second portions. In various embodiments, the first portion 202 opens to the first major surface 410. In additional embodiments, the first portion 202 has a depth of t1, and the second portion 206 has a depth which is the distance of the depth t1 subtracted from the thickness of the plate 110.

In various embodiments, the aperture is adapted to mate with a plug, as is demonstrated by the plate 110 and the plug 108 of the exemplary illustration of FIG. 2. In various embodiments, the plug 108 roughly matches the shape defined by the first portion 202 of the aperture 414. In embodiments using the plug to form a seal with the aperture, a plug is selected which includes a thickness which is approximately equal to the thickness t1. In various embodiments, the surface of the plug is roughly coplanar with the surface of the plate once installed. Various examples of the present subject matter affix the plug to the plate 110 using welding, an interference fit, adhesive, threads, or various additional forms of attachment. On embodiment uses laser welding. In one embodiment, the weld is performed by an approximately 1064 nm Yag laser weld with an energy range of approximately 1.5 joules to 2.5 joules.

In various embodiments, the plate is adapted to mate with an opening in a case 114, as illustrated in the example of FIG. 1. For instance, in one embodiment, the plate is shaped to restrict its passage through an opening in the case 114. Accordingly, one example of the plate includes a step 402 which divides the plate into a first section with a first major surface 410, and a second section with a second major surface 412. In one embodiment, the first major section 410 is sized for passage through an opening in a case 114, and the second major section is sized so that it cannot pass through the same opening. In one embodiment, the face of the step 402 is positioned proximal to an interior surface of case 114, and is further positioned proximal to an opening in the case 114.

In various embodiments, the plate includes a thickness t2. In various embodiments, the thickness t2 is selected to match the thickness of a capacitor case, including the case illustrated in the example of FIG. 1. In examples where t2 matches the thickness of a capacitor case, the major face 110 is coplanar with the exterior of a capacitor case when the plate 110 is attached to the capacitor case.

Generally, the thickness of the plate 110 depends on the type and nature of the contents of the capacitor. In general, a thickness is chosen which is compatible with desired manufacturing processes. For example, in embodiments where a conductor is welded to the plate 110, a plate thickness is chosen which will result in a final plate shape, after welding, which is substantially similar to the shape of the plate prior to the welding process. In other words, in various embodiments, the thickness of the plate is selected to minimize warpage due to thermal stress applied to the plate 110 due to various processes, including welding.

In general, the plate can be manufactured by machining, powdered metallurgy, or by stamping. Additional forming processes are also within the scope of the present subject matter. In various embodiments, the transition between the first portion 202 of the aperture and the second portion of the aperture 206 is designed with the objective of enabling laser welding. In some examples, enabling a laser weld requires that the transition include step shapes which are largely perpendicular. Varying embodiments of a laser welding process require a step shape to limit laser energy from extending beyond the welding area. In one embodiment, the weld is performed by an approximately 1064 nm Yag laser weld with an energy range of approximately 1.5 joules to 2.5 joules.

Figure 5:
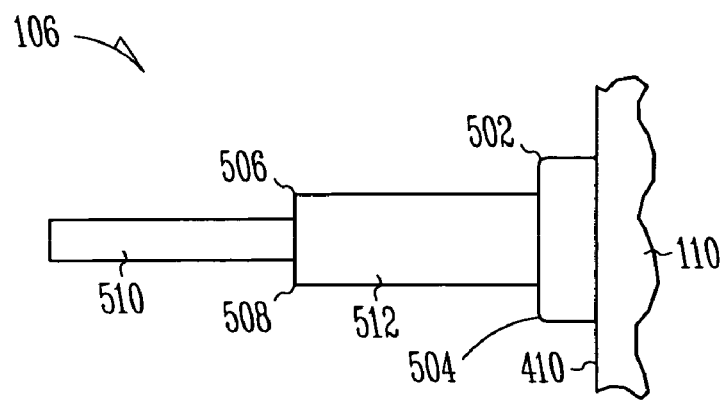
FIG. 5 shows a side view of conductor attached to a plate with a first major face, according to one embodiment of the present subject matter.

FIG. 5 shows a side view of conductor 106 attached to a plate 110 with a first major face 410, according to one embodiment of the present subject matter. In various embodiments, the conductor 106 includes a wire 510 and a coupling member 512, and one or more arc percussion welding areas, 506, 508, 502 and 504. In various embodiments, the wire 510 is attached to the coupling member 512 using a crimping process, a welding process, or other processes. In one embodiment, the coupling member 512 is arc percussion welded to the wire at one or more areas. In various examples, areas 506 and 508 are used for applying an arc-percussion weld. Additionally, the coupling member 512 is arc-percussion welded to a plate 110 in various embodiments, and in one embodiment the coupling member 512 is arc percussion welded at areas 502 and 504. Because of the nature of arc percussion welding, the mating region between the plate 110 and the coupling member 512 must be chosen to enable a desired form of weld. In one example, coupling member 512 and plate 110 include substantially planar faces which are adapted to mate with each other.

An exemplary arc percussion welding machine is manufactured by Morrow Tech Industries of Broomfield, Colo. In this embodiment, the conductor 510 and coupling members are not crimped together. However, some embodiments include both welding and crimping.

In further embodiments, the weld connection is formed using resistance welding. In one example, a conductor is held to a plate with a clamping force of from about 5 to 15 pounds. In the example, the welding process uses a current of from about 350 to 500 Amps. The ramp time in the example is from about 5 to 15 milliseconds. The time for the weld in the example is from about 5 to 15 milliseconds. The gas flow for the example process is from about 0 to 8 standard cubic feet per hour.

It should be noted that in some embodiments, the wire 510 and the coupling member are one piece. Additionally, it should be noted that other forms of conductor 106 which are adapted for percussion welding to a plate 110 are within the scope of the present subject matter.

Figure 6:
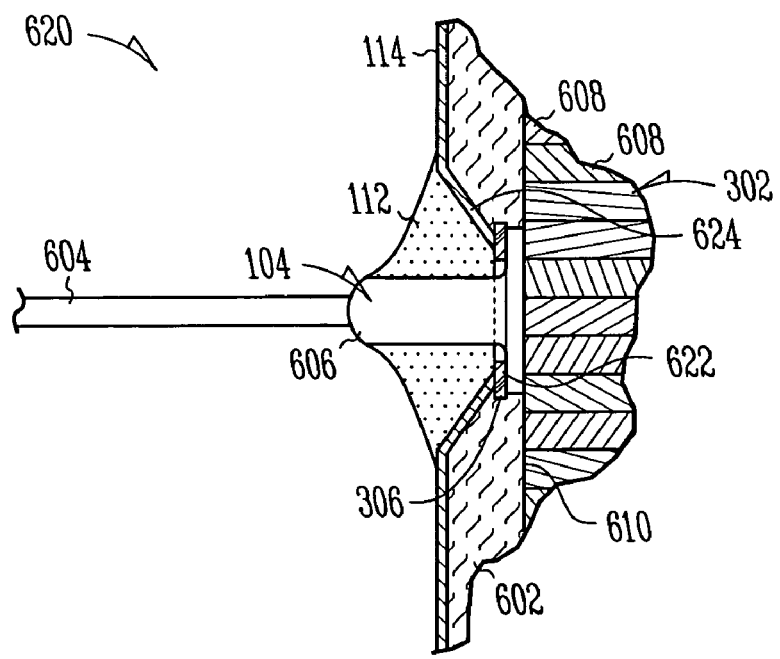
FIG. 6 shows a cross-sectional side view of a feedthrough assembly, according to one embodiment of the present subject matter.

FIG. 6 shows a cross-sectional side view of details of one embodiment of feedthrough assembly 620. In some examples, a means is available for connecting the capacitor stack contained in the case to electronics which are located outside of the case. In some of these embodiments, the connecting means is of one polarity, and the capacitor case is of another polarity. In these embodiments, it is necessary to provide a structure for allowing electricity to pass through the case wall without contacting the case wall. In various embodiments, the feedthrough assembly 620 demonstrates one embodiment adapted for providing this. In varying examples, the feedthrough assembly 620 includes a feedthrough passageway 308 which is drilled, molded, punched, or otherwise formed in a portion of a sidewall of the case 114. Additionally, in some embodiments, the feedthrough passageway is located in a plate, or is located partially in a case and partially in a plate. For example, in one embodiment, one half of a feedthrough passageway is located in a plate or cover and one half of a feedthrough passageway is located in a case.

In some embodiments, the feedthrough assembly 620 includes an anode conductor 104 which is attached to the anode of the capacitor. Varying embodiments of the capacitor anode include one or more anode members 608 which are coupled to anode conductor 104 for electrically connecting the anode to circuitry outside the case 114. In one embodiment, anode members 608 are edge-welded to each other. Edge-welding the anode members 608, in various embodiments, provides a flat connection surface 410. In some embodiments, anode members 608 are crimped or soldered, and in further embodiments, the anode members 608 are connected by an electrically conductive adhesive or by other means.

In some embodiments, a wire 604 is coupled to a coupling member 606, forming, in part, an anode conductor 104. Various embodiments of the present subject matter include attaching the wire 604 to the coupling member 606 using soldering, welding, crimping, and other methods sufficient to connect the wire 604 to the coupling member 606, in varying embodiments. In one embodiment, anode conductor 104 is a single, substantially unified metallic crystalline member.

In one embodiment, coupling member 606 is a high-purity aluminum member which is able to withstand the high voltages generated within the capacitor case. In other embodiments it is made from another conductive material compatible with the capacitor stack 302. In various embodiments, one side of the coupling member 606 includes a planar surface for attaching to the planar surface 610 presented by edge-welded capacitor stack 608.

In one embodiment, coupling member 606 is laser welded to surface 610 of capacitor stack 302 using a butt-weld. Alternatively, coupling member 606 is attached using other means. Butt-welding coupling member 606 directly to capacitor stack 302 provides an electrical connection between capacitor stack 302 and the conductor. Also, since coupling member 606 is directly attached to capacitor stack 302, it supports the conductor while a curable resin 112, such as an epoxy, is applied to the feedthrough passageway area.

In one embodiment, feedthrough passageway 308 is in part defined by an edge which is tapered to improve the surface area available to a bonding agent. Curable resins bond to surfaces, and as such, can create a larger bonding areas when applied to a larger surface area. A larger bond, in various embodiments, is more robust, reliable, and is less likely to permit leaks. Additionally, in one embodiment, a larger bonding area can increase the distance between the coupling member and the case by including a larger feedthrough passage. Accordingly, increased area can reduce instances of unwanted arcing. A tapered edge, in various embodiments, includes these benefits. For example, in one embodiment, a feedthrough passageway includes an inbound narrowing sidewall 624 extending to a lip 622. In various embodiments, a cavity is defined by the sidewall 624, the coupling member 606, and an isolating element 306. A curable resin 112, in various embodiments, is disposed in the cavity and hardened, and serves to insulate the case 114 from the anode conductor 104, and further serves as a seal to resist the flow of electrolyte 602. For example, in one embodiment, the conductor is an uninsulated anode conductor 104 connected to the anode of the capacitor stack, the anode conductor 104 passing through a feedthrough passageway 308 in a cathodic case 114. In this exemplary embodiment, a curable resin 112 is used to seal electrolyte 602 into the capacitor, and is further used to insulate the anodic elements, such as the coupling 606, from the cathodic elements, such as the case 114. In one example, the curable resin 112 is a hardened two-part quick-setting thermal-set epoxy.

In one embodiment, an isolating element 306 is combined with the conductor 104, the feedthrough passageway 308, and the curable resin 112. This combination, in various embodiments, in useful for restricting the flow of electrolyte 602, curable resin 112, or both. In various embodiments, the isolating element 306 is a paper washer which assists in limiting the flow of curable resin 112 to a desired area. One benefit of using an isolating element 306 to restrict the flow of a curable resin, such as epoxy, is that the epoxy is less likely to flow into other locations within the capacitor, which can adversely affect capacitor performance.

In varying embodiments, the feedthrough passageway 308 is assembled to the capacitor stack and seals to the capacitor stack surface 610, and in additional embodiments, the feedthrough passageway 308 seals to the coupling member 606. In one embodiment, the feedthrough passageway 308 includes a lip 622 adapted for forming a circular seal with the coupling member 606. In various embodiments, because of the nature of assembly, including imperfect manufacturing tolerances and imperfect surface finishes, the effectiveness of the seal formed between the feedthrough passageway 308 and the coupling member 606 is limited. To increase the effectiveness of the seal, in various embodiments, an isolating element 306 is located between the feedthrough passageway 308 and the coupling member 606 which is compressible, and which resists the flow of electrolyte and resists the flow of epoxy. In one embodiment, the isolating element 306 is constructed from paper which is of a thickness which can absorb manufacturing irregularities, such as surface finish irregularities and manufacturing tolerance irregularities, while providing a seal.

In additional embodiments, the isolating element 306 is useful for providing electrical insulation between the case 114 and the anode conductor 104. In varying embodiments, the element is made out of separator paper, and in one example, it is made out of kraft paper. For example, in various embodiments, the case is cathodic, and an anodic coupling 606 must be electrically isolated from the case 114 for the capacitor to function. Additionally, in various embodiments, to reduce the size of the capacitor, the anode conductor 104 and the case 114 are placed near one another. Therefore, in various embodiments, to reduce instances of arc between the case an the anodic conductor 104, an insulative element 306 is disposed between the case 114 and the anode conductor 104.

In various embodiments, a curable resin 112 is any of numerous clear to translucent yellow or brown, solid or semisolid, viscous substances of plant origin, such as copal, rosin, and amber, used principally in lacquers, varnishes, inks, adhesives, synthetic plastics, and pharmaceuticals. Additionally, curable resin 112 includes any of numerous physically similar polymerized synthetics or chemically modified natural resins including thermoplastic materials such as polyvinyl, polystyrene, and polyethylene and thermosetting materials such as polyesters, epoxies, and silicones that are used with fillers, stabilizers, pigments, and other components to form plastics. It should be noted that the sealing members listed here are not a complete list of the sealing members within the scope of the present subject matter. For example, various examples include sealing members which provide a non-hermetic seal, and one embodiment includes a substantially elastic plug.

An exemplary curable resin 112 is an epoxy which is a two-part epoxy manufactured by Dexter Hysol. This includes a casting resin compound (manufacturer No. EE 4183), a casting compound (manufacturer No. EE), and a hardener (manufacturer No. HD 3404). The exemplary two-part epoxy is mixed in a ratio of hardener=0.055*casting resin. The mixture is cured at 0.5 hours at 60 degrees Celsius or 1.5 hours at room temperature. Another epoxy is a UV cure epoxy such as manufactured by Dymax, Inc., which can be cured using an Acticure (manufactured by GenTec) ultraviolet curing system at 7 W/cm$^2$ at a distance of 0.25 inches for approximately 10 seconds.

It should be noted that the embodiments enumerated here, in which an anode conductor passes through a feedthrough assembly, are only examples of the present subject matter. Additional embodiments include a cathode conductor passing through a passageway in an anodic capacitor case. Further, additional embodiments include multiple feedthrough passages, and some include a case which is neither anodic nor cathodic.

Figure 7:
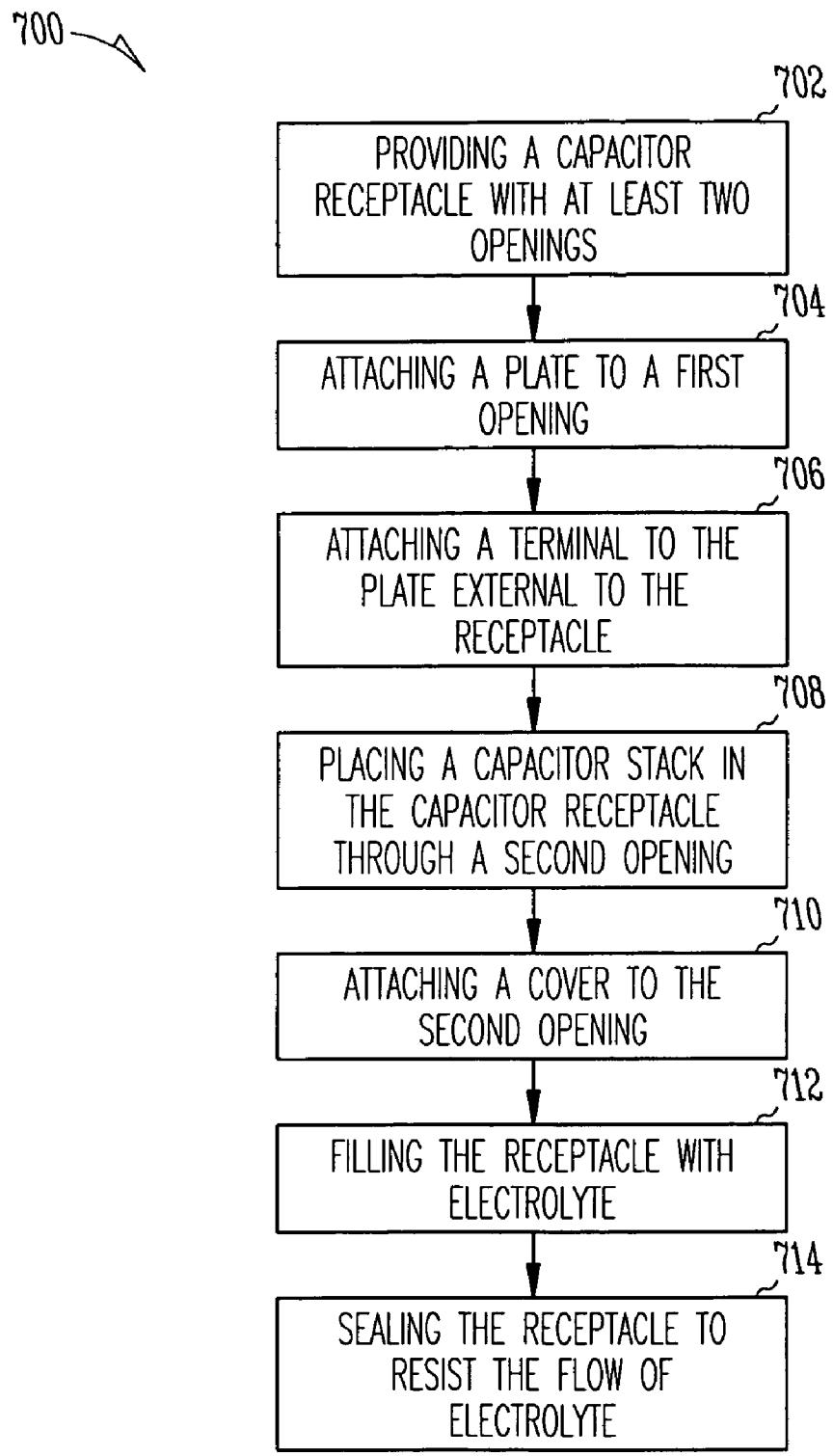
FIG. 7 shows a method for manufacturing an implantable defibrillator according to one embodiment of the present subject matter.

FIG. 7 shows a method 700 for manufacturing an implantable cardioverter defibrillator according to one embodiment of the present subject matter. In various embodiments, the method includes providing a capacitor receptacle with at least two openings 702. For example, various embodiments include a cup-shaped receptacle, with a major surface and side-walls extending from the surface and forming a dish-shaped volume. In one embodiment, the receptacle side-walls include two openings: a first opening which is adapted for mating with a plate, and a second opening which is adapted for mating with a cover. In various embodiments, the receptacle is a conductive metal, and in one embodiment, the receptacle is aluminum.

In various embodiments, the method includes attaching a plate to one of the openings in the receptacle 704. In various examples, the plate is sized for mating with the first opening. In some examples, the plate is substantially planar, and cannot pass through the first opening when positioned approximately parallel to the sidewall which includes the opening. Additionally, in various embodiments, the plate is sized thicker than the sidewall of the receptacle. In embodiments where the sidewall is not of a uniform thickness, the plate is thicker than at least part of the sidewall proximal to the opening to which the plate is attached.

Varying embodiments attach the plate using a welding process. In one embodiment, the plate is attached using a laser welding process. In one embodiment, the weld is performed by an approximately 1064 nm Yag laser weld with an energy range of approximately 1.5 joules to 2.5 joules. In other embodiments, the plate is attached to the receptacle using other means, such as threads or a mechanical lock. In various forms, attaching the plate to the receptacle forms a seal, and in some embodiments the seal resists the flow of electrolyte.

Various embodiments of the present subject matter include a plate adapted for attachment of a terminal. Various embodiments include attaching a terminal to the plate 706. For example, in various embodiments, a terminal is welded to the plate. In one embodiment, a terminal is percussion welded to the plate. In various embodiments, the parameters of the percussion weld require a plate of a minimum thickness, and the plate is sized to approximate that thickness. By sizing the plate to approximately match the required parameters of the welding process, only a portion of the capacitor case is produced at that thickness, allowing the remaining portions, which are not welded, to be thicker or thinner. In one embodiment, a thinner receptacle is used, which results, in various embodiments, in a capacitor which is smaller and lighter.

In various examples, a capacitor stack is placed in the capacitor receptacle through the second opening 708. Additionally, various embodiments include attaching a cover to the second opening 710. Attaching the cover includes, in various embodiments, welding the cover to the receptacle. In one embodiment, a seal is created using a laser welding process which resists the flow of electrolyte.

Various embodiments also include filling the receptacle with electrolyte 712, and sealing the receptacle to resist the flow of electrolyte 714. For example, in one embodiment, an aperture provides access to the interior volume formed by attaching the plate and the cover to the receptacle. In various embodiments, the aperture is the only access to the interior of the capacitor case which does not resist the flow of electrolyte. In various embodiments, the method of the present subject matter includes filling the volume with electrolyte. For example, in various embodiments, the volume is filled, and later pressurized to encourage the escape of gasses from the interior volume of the capacitor. In one embodiment, the gases escape through the aperture. Various embodiments include sealing the aperture after the capacitor has been filled with electrolyte to resist the flow of electrolyte.

Figure 8:
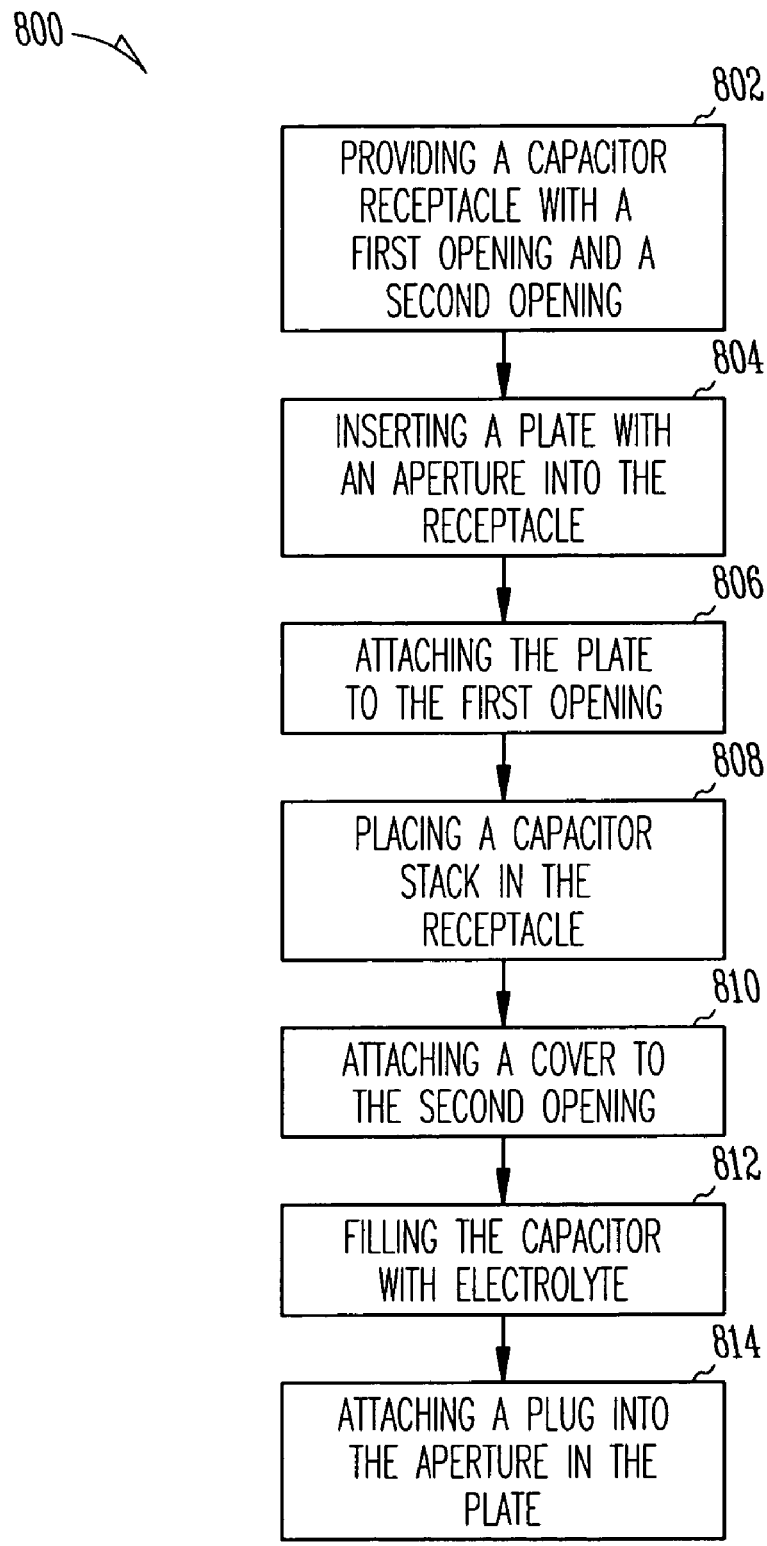
FIG. 8 shows a method for manufacturing an implantable defibrillator according to one embodiment of the present subject matter.

FIG. 8 shows a method 800 for manufacturing an implantable cardioverter defibrillator, according to one embodiment of the present subject matter. For example, in various embodiments, a receptacle is provided with a first opening and a second opening 802. In some embodiments, a plate is inserted 804 into the receptacle and attached 806 to the first opening. In one embodiment, the plate is substantially planar and is sized so that it cannot pass through the first opening when positioned approximately parallel to the plate formed by the perimeter of the opening.

In various embodiments, the plate includes an aperture. In one embodiment, the plate is inserted and attached to the receptacle, a capacitor stack is installed in the receptacle 808, and a cover is attached to the receptacle 810. The exemplary embodiment is assembled forming a seal which resists the flow of electrolyte, excluding the aperture. Various examples which are sealed to resist the flow of electrolyte are filled with electrolyte 812, which substantially impregnates the interior volume of the capacitor case. Various examples use a pressure differential to encourage the impregnation of the interior volume of the capacitor with electrolyte.

Various examples plug the aperture with a member 814, which can be attached in a number of ways, including welding, interference fit, threading, and other means suitable for forming a sealed attachment. In one embodiment, the aperture is sealed by laser welding a disc shaped plug into a similarly shaped counterbore in the aperture.

Figure 9:
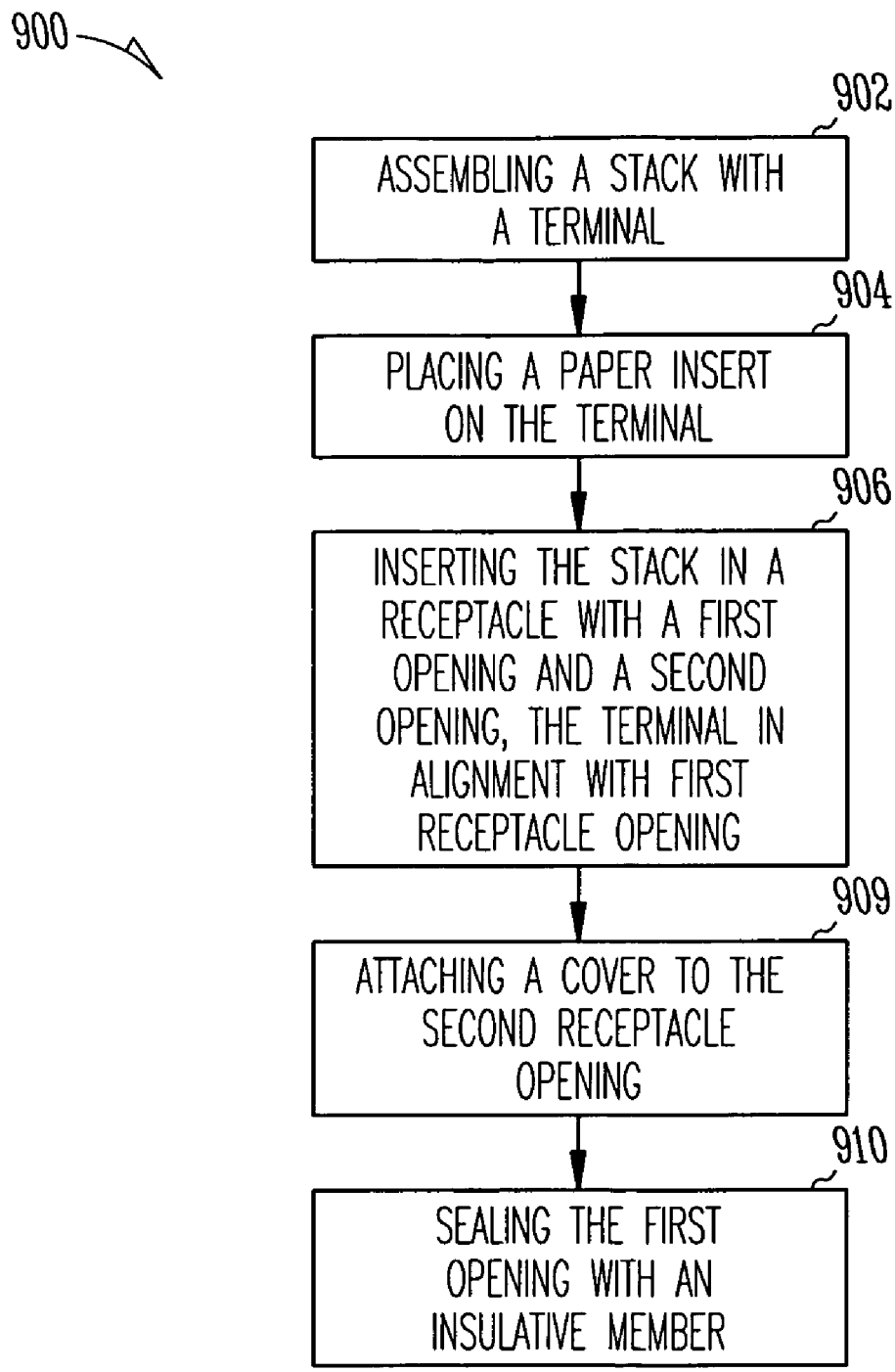
FIG. 9 shows a method for manufacturing an implantable defibrillator according to one embodiment of the present subject matter.

FIG. 9 shows a method 900 for manufacturing an implantable cardioverter defibrillator according to one embodiment of the present subject matter. In various embodiments, the method of the present subject matter includes assembling a stack with at least one terminal 902. In various embodiments, a paper isolating element 306 is assembled to the terminal 904. In one exemplary embodiment of the present subject matter a paper washer is inserted onto a terminal which is shaped like a boss.

In various embodiments, the assembled capacitor stack is placed into a receptacle with a first opening and a second opening 906. Various examples of the method of the present subject matter include aligning the terminal with the first receptacle opening. One example includes aligning the terminal with the first receptacle opening so that the terminal passes at least part of the way through the receptacle opening.

Various embodiments attach a cover to the second receptacle opening 909. Various embodiments include attaching the cover using a welding process, including laser welding. Additional embodiments include attaching the cover with various additional methods, including using mechanical locks, rivets, fasteners, or other forms of fastening methods. In various embodiments, attaching the cover to the second receptacle opening includes forming a seal between the cover and the receptacle. In one example, the seal is adapted for resisting the flow of electrolyte.

In various embodiments, a sealing member is used to seal the terminal to the first opening 910. For example, in various embodiments, an epoxy is used to seal the space between the terminal and the first opening. In one exemplary embodiment of the present subject matter the paper isolating element 306 is adapted to interface with the first opening and the terminal to form a seal which is adapted to localize the epoxy proximal to the interface between the paper insert, the terminal, and the second opening. In other words, the paper isolating element 306 is adapted to limit the epoxy to wetting proximal to the terminal, the first opening, and the paper insert.

It should be noted that the methods of the present subject matter, in various embodiments, include inserting the assembled capacitor into an implantable medical device suited for delivering electrical stimulation to a patient. In one embodiment, the method of the present subject matter includes installing a capacitor in a implantable cardioverter defibrillator which is adapted for implant in a patient, and which is also adapted to deliver high voltage pulses to a patient in order to promote cardiac wellness. For example, in various embodiments, one method of the present invention includes providing a defibrillator case having circuitry disposed in the case. Additionally, various embodiments include implanting an implantable cardioverter defibrillator in a patient. Also, some examples include connecting the cardiac system of a patient to the implantable cardioverter defibrillator. In one example, circuitry in the capacitor controls the discharge of electrical energy from the capacitor to the patient. Overall, in various embodiments, the method of the present invention enables improved delivery of electrical stimulation to a patient using an implantable cardioverter defibrillator.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

We claim:

1. A feedthrough assembly with a cavity, comprising:
  a capacitor stack, including one or more substantially flat anode layers and one or more substantially flat cathode layers;
  a case having a first opening sized for passage of the capacitor stack and a second opening, the second opening defined by a lip, the capacitor stack disposed in the case;
  a conductive member attached to the capacitor stack, the conductive member disposed at least part way through the second opening in the case;
  an isolating element disposed between the lip and at least a portion of the connected stack and conductive member, the isolating element adapted to electrically isolate the lip and the connected stack and conductive member;
  a curable resin sealingly disposed in the cavity defined by the second opening, the isolating element, and the conductive member, the curable resin electrically isolating the case from the conductive member, and
  a cover substantially conforming to the first opening and sealingly connected to the first opening.

2. The feedthrough assembly of claim 1, wherein the second opening in the case is narrowing.

3. The feedthrough assembly of claim 2, wherein the second opening is funnel-shaped.

4. The feedthrough assembly of claim 1, wherein the case includes a third opening, and a plate substantially conforming to the third opening, and sealingly connected to the case.

5. The feedthrough assembly of claim 4, wherein the case and the plate are in electrical communication.

6. The feedthrough assembly of claim 5, wherein the plate is adapted for attachment of a terminal, and wherein the terminal is connected to the plate and is in electrical connection with the case and at least one capacitor electrode.

7. The feedthrough assembly of claim 4, wherein the plate includes an aperture.

8. The feedthrough assembly of claim 7, wherein a plug is sealingly connected to the aperture.

9. The feedthrough assembly of claim 1, wherein the receptacle includes an aperture.

10. The feedthrough assembly of claim 9, wherein a plug is sealingly connected to the aperture.

11. The feedthrough assembly of claim 9, wherein the isolating element is washer shaped, including a first major face and a second major face, the first major face abutting the narrowing opening, the second major face abutting the base of the conductive element.

12. The feedthrough assembly of claim 1, wherein the insulative member is paper.

13. The feedthrough assembly of claim 12, wherein the insulative member is made from kraft paper.

14. The feedthrough assembly of claim 1, wherein the curative resin is an epoxy.

15. The feedthrough assembly of claim 1, wherein the curative resin forms a hermetic seal with the case.

16. A feedthrough assembly with a cavity, comprising:
  a capacitor stack, including one or more substantially flat anode layers and one or more substantially flat cathode layers;
  an electrically conductive case having a first opening sized for passage of the capacitor stack, a narrowing second opening formed in the exterior surface of the electrically conductive case with a narrow end internal to the case including a lip, and a third opening, the capacitor stack disposed in the case;
  a plate with an aperture substantially conforming to the third opening, and sealingly connected to the case in electrical communication with the case;
  a plug sealingly connected to the aperture in the plate;
  a terminal attached to the plate;
  a conductive member including an elongate first section and a base, the conductive member attached to the capacitor stack at the base, the elongate first section disposed at least part way though the second opening in the case;
  an isolating element disposed between the lip and the base of the conductive member;
  a curable resin sealingly disposed in the cavity formed by the second opening, the isolating element, and the conductive member, the curable resin adapted to electrically isolate the case from the conductive member; and
  a cover substantially conforming to the first opening and sealingly connected to the first opening.

17. The feedthrough assembly of claim 16, wherein the insulative member is paper.

18. The feedthrough assembly of claim 17, wherein the insulative member is made from kraft paper.

19. The feedthrough assembly of claim 16, wherein the curative resin is an epoxy.

20. A method of making a feedthrough assembly with a cavity, comprising:
    assembling a capacitor stack out of substantially layered electrodes;
    attaching a conductive member to the capacitor stack;
    assembling an isolating element to the connected capacitor stack and conductive member;
    inserting the stack in a receptacle with a first opening sized for passage of a capacitor stack and a second opening defined by a lip, the conductive member in alignment with the second opening, the isolating element disposed between the lip and the conductive member, filling the cavity with curable resin, the cavity defined by the second opening, the isolating element, and the conductive member;
    curing the resin; and
    sealing a cover to the first receptacle opening.

21. The method of claim 20, wherein the receptacle includes a feedthrough aperture, and the capacitor is impregnated with electrolyte flowing through the aperture.

22. The method of claim 21, wherein the aperture is sealed with a plug.

23. The method of claim 22, further comprising using a laser to seal the plug to the aperture.

24. The method of claim 21, wherein the aperture includes a counter-bore.

25. The method of claim 24, wherein a plug shaped to conform to the counter-bore is sealed to the counterbore.

26. The method of claim 20, wherein the receptacle includes a third opening and a plate sealed to the third opening.

27. The method of claim 26, wherein a terminal is connected to the plate.

28. The method of claim 26, wherein the plate includes a feedthrough aperture, and the capacitor is impregnated with electrolyte flowing through the aperture.

29. The method of claim 28, wherein the aperture is sealed with a plug.

* * * * *

UNITED STATES PATENT AND TRADEMARK OFFICE
CERTIFICATE OF CORRECTION

PATENT NO. : 7,408,762 B2  Page 1 of 1
APPLICATION NO. : 11/182729
DATED : August 5, 2008
INVENTOR(S) : Taller et al.

It is certified that error appears in the above-identified patent and that said Letters Patent is hereby corrected as shown below:

In column 14, line 58, in Claim 16, delete "though" and insert -- through --, therefor.

Signed and Sealed this

Eleventh Day of November, 2008

JON W. DUDAS
*Director of the United States Patent and Trademark Office*